United States Patent
Koob et al.

(10) Patent No.: US 11,077,122 B2
(45) Date of Patent: Aug. 3, 2021

(54) NON-BIOCONVERTIBLE C$_3$-SUBSTITUTED PREGNENOLONE DERIVATIVES FOR USE IN THE TREATMENT OF SUBSTANCE USE DISORDERS

(71) Applicant: MAPREG, Le Kremlin Bicetre (FR)

(72) Inventors: George F. Koob, Rancho Santa Fe, CA (US); Barbara Jean Mason, Rancho Santa Fe, CA (US); Olivier George, Lemon Grove, CA (US); Etienne Baulieu, Paris (FR); Isabelle Villey, Colombes (FR)

(73) Assignee: MAPREG, Le Kremlin Bicetre (FR)

( * ) Notice: Subject to any disclaimer, the term of this patent is extended or adjusted under 35 U.S.C. 154(b) by 0 days.

(21) Appl. No.: 15/773,798

(22) PCT Filed: Nov. 4, 2016

(86) PCT No.: PCT/EP2016/076741
§ 371 (c)(1),
(2) Date: May 4, 2018

(87) PCT Pub. No.: WO2017/077082
PCT Pub. Date: May 11, 2017

(65) Prior Publication Data
US 2018/0318317 A1 Nov. 8, 2018

(30) Foreign Application Priority Data
Nov. 6, 2015 (EP) ..................................... 15306765

(51) Int. Cl.
*A61K 31/57* (2006.01)
*A61P 25/32* (2006.01)

(52) U.S. Cl.
CPC .............. *A61K 31/57* (2013.01); *A61P 25/32* (2018.01)

(58) Field of Classification Search
CPC ................................ A61K 31/57; A61P 25/32
See application file for complete search history.

(56) References Cited

U.S. PATENT DOCUMENTS

| 2013/0244991 | A1* | 9/2013 | Baulieu | .................. | A61K 31/57 514/182 |
| 2014/0228336 | A2 | 8/2014 | Baulieu et al. | | |

FOREIGN PATENT DOCUMENTS

| WO | 2004067010 A1 | 8/2004 | |
| WO | 2012160006 A1 | 11/2012 | |
| WO | WO-2012160006 A1 * | 11/2012 | ............ C07J 7/0045 |

OTHER PUBLICATIONS

Suter et al., "Depressive symptoms as a predictor of alcohol relapse after residential treatment programs for alcohol use disorder," Journal of Substance Abuse Treatment 41 (2011) 225-232.*
Kuria et al., "The Association between Alcohol Dependence and Depression before and after Treatment for Alcohol Dependence," ISRN Psychiatry, vol. 2012.*
Nunes et al., "Treatment of Depression in Patients with Alcohol or other Drug Dependence A Meta-analysis," JAMA Apr. 21, 2004, vol. 291, No. 15.*
Rapinesi et al., "Antidepressant effectiveness of deep Transcranial Magnetic Stimulation (dTMS) in Patients with Major Depressive Disorder (MDD) with or without Alcohol Use Disorders (AUDs): A 6-month, open-label, follow-up study," Journal of Affective Disorders (2014).*
DeVido et al., "Treatment of the Depressed Alcoholic Patient," Curr Psychiatry Rep. Dec. 14, 2012(6): 610-618.*
Airov, "Antidepressants Appear Effective for Comorbid MDD and AUD," American Psychiatric Association Annual Meeting (May 19, 2019).*
Winslow et al., Am Fam Physician. Mar. 15, 2016;93(6):457-465, explains: "Antidepressants do not decrease alcohol use in patients without mood disorders, but sertraline and fluoxetine may help depressed patients decrease alcohol ingestion."*
Addolorato et al., "Novel therapeutic strategies for alcohol and drug addiction: focus on GABA, ion channels and transcranial magnetic stimulation," Neuropsychopharmacology, Jan. 2012, 37(1):163-177.
Besheer et al., "Pregnenolone and ganaxolone reduce operant ethanol self-administration in alcohol-preferring P rats," Alcohol Clin Exp Res., Dec. 2010, 34(12):2044-2052.
Gilpin et al., "Operant behavior and alcohol levels in blood and brain of alcohol-dependent rats," Alcohol: Clin Exp Res., 2009, 33:2113-2123.
Heilig et al., "A key role for corticotropin-releasing factor in alcohol dependence," Trends Neurosci., 2007, 30:399-406.
Koob et al., "Review Neurobiological mechanisms for opponent motivational processes in addiction," Philos Trans R Soc Lond B Biol Sci., Oct. 12, 2008, 363(1507):3113-3123.
Koob et al., "Development of pharmacotherapies for drug addiction: a Rosetta stone approach," Nature Rev Drug Discov., 2009, 8:500-515.
Koob et al., "Neurocircuitry of addiction," Neuropsychopharmacology, Jan. 2010, 35(1):217-238.
Le Foll et al., "Cannabinoid CB1 receptor antagonists as promising new medications for drug dependence," J Pharmacol Exp Ther, Mar. 2005, 312(3):875-883.
Lowery et al., "Pre-clinical evidence that corticotropin-releasing factor (CRF) receptor antagonists are promising targets for pharmacological treatment of alcoholism," CNS Neurol Disord Drug Targets, Mar. 2010, 9(1):77-86.
Olive et al., "Glutamatergic medications for the treatment of drug and behavioral addictions," Pharmacol Biochem Behav., Feb. 2012, 100(4):801-810.

(Continued)

*Primary Examiner* — Jared Barsky
(74) *Attorney, Agent, or Firm* — Arrigo, Lee, Guttman & Mouta-Bellum LLP

(57) ABSTRACT

The present invention relates to the use of non-bioconvertible C$_3$-substituted pregnenolone derivatives of formula (I), with no significant affinity for hormonal receptors or receptors of the central nervous system, in the treatment of substance use disorders, and in particular of alcohol use disorder.

5 Claims, 7 Drawing Sheets

(56) References Cited

OTHER PUBLICATIONS

O'Dell et al., "Enhanced alcohol self-administration after intermittent versus continuous alcohol vapor exposure," Alcohol: Clin Exp Res., 2004, 28:1676-1682.

Richardson et al., "MPZP: a novel small molecule corticotropin-releasing factor type 1 receptor (CRF1) antagonist," Pharmacol Biochem Behav., 2008, 88:497-510.

Rimondini et al., "Long-lasting increase in voluntary ethanol consumption and transcriptional regulation in the rat brain after intermittent exposure to alcohol," Faseb J., 2002, 16:27-35.

Roberts et al., "Operant self-administration of sweetened versus unsweetened ethanol: effects on blood alcohol levels," Alcohol: Clin Exp Res., 1999, 23:1151-1157.

Roberts et al., "Excessive ethanol drinking following a history of dependence: animal model of allostasis," Neuropsychopharmacology, 2000, 22:581-594.

Vanyukov et al., "Liability to substance use disorders: 1. Common mechanisms and manifestations," Neurosci Biobehav Rev., Oct. 2003, 27(6):507-515.

Walker et al., "Targeting dynorphin/kappa opioid receptor systems to treat alcohol abuse and dependence," Alcohol, Jun. 2012, 46(4):359-370.

Odell et al., "Epipregnanolone and a novel synthetic neuroactive steroid reduce alcohol self-adminisration in rats" Pharmacology Biochemistry and Behavior, Jul. 1, 2005, 81(3):543-550.

Barbosa et al., "Effect of epipregnanolone and pregnenolone sulfate on chronic tolerance to ethanol" Pharmacology Biochemistry and Behavior, Nov. 1, 2000, 67(3):459-464.

Adamson et al., "A Randomized Trial of Combined Citalopram and Naltrexone for Nonabstinent Outpatients With Co-Occurring Alcohol Dependence and Major Depression," Journal of Clinical Psychopharmacology, vol. 35, No. 2, Apr. 2015, pp. 143-149.

Charney et al., "Poorer Drinking Outcomes with Citalopram Treatment for Alcohol Dependence: A Randomized, Double-Blind, Placebo-Controlled Trial," Alcohol Clin Exp Res, vol. 39, No. 9, 2015, pp. 1756-1765.

Pettinati et al., "Current Status of Co-Occurring Mood and Substance Use Disorders: A New Therapeutic Target," Am J Psychiatry, vol. 170, Issue 1, Jan. 1, 2013, pp. 23.30.

Nunes et al. (2004), "Treatment of depression in patients with alcohol or other drug dependence: a meta-analysis," JAMA, 291(15), 1887-96.

Lovieno et al. (2011), "Antidepressants for major depressive disorder and dysthymic disorder in patients with comorbid alcohol use disorders: a meta-analysis of placebo-controlled randomized trials," J Clin Psychiatry, 72(8),1144-51.

Boden et al. (2011), "Alcohol and depression," Addiction, 106(5), 906-14.

* cited by examiner

NON-BIOCONVERTIBLE C₃-SUBSTITUTED PREGNENOLONE DERIVATIVES FOR USE IN THE TREATMENT OF SUBSTANCE USE DISORDERS

TECHNICAL FIELD OF THE INVENTION

The present invention is in the field of treatment of substance use disorders. It relates to the use of particular derivatives of pregnenolone, which are blocked in $C_3$ position and cannot metabolize in vivo into pregnenolone derivatives and which do not have significant affinity for steroid hormonal receptors and for all tested classical main receptors and receptors of neurotransmitters of the central nervous system, for the treatment of substance use disorders.

BACKGROUND ART

Substance use disorders (SUDs) are a group of complex behavioral and chronically relapsing disorders characterized by the presence of (1) loss of control, (2) social impairment, (3) risky use of the substance, and/or (4) pharmacological tolerance and withdrawal. SUDs lead to significant health and public order problems, and treatments of these disorders are highly desirable.

At the biological level, SUDs are characterized by alteration of several neurological signaling pathways, and various treatments aiming to restore normal signaling have been proposed. In particular:

SUDs are known to alter γ-aminobutyric acid (GABA) neurotransmission, and negative allosteric modulators of the $GABA_A$ receptor, and $GABA_B$ direct agonists such as baclofen or $GABA_B$ positive allosteric modulators have been proposed for the treatment of SUDs (Addolorato G et al. Neuropsychopharmacology. 2012 January; 37(1):163-77). Gabapentin also increases GABA neurotransmission, which may also explain its effect on SUDs. Topiramate, a glutamatergic compound, also increases $GABA_A$-facilitated neuronal activity, which may also explain its effect on SUDs (Addolorato G et al. Neuropsychopharmacology. 2012 January; 37(1):163-77). In this respect, ganaxolone, a synthetic GABAergic steroid, and pregnenolone, a precursor of all GABAergic neuroactive steroids in vivo, have also been shown to reduce operant ethanol self-administration in alcohol-preferring P rats (Besheer J, et al. Alcohol Clin Exp Res. 2010 December; 34(12): 2044-52).

SUDs are also known to alter cannabinoid CB1 receptor signaling, and CB1 receptor antagonists have been proposed for treatment of SUDs (Le Foll B, Goldberg S R. Cannabinoid CB1 receptor antagonists as promising new medications for drug dependence. J Pharmacol Exp Ther. 2005 March; 312(3):875-83; WO2012160006A1).

SUDs are also known to alter glutamatergic transmission and glutamatergic compounds (acamprosate, N-acetylcysteine, D-cycloserine, gabapentin, lamotrigine, memantine, modafinil, and topiramate) have been proposed for treatment of SUDs (Olive M F et al. Pharmacol Biochem Behav. 2012 February; 100(4):801-10).

SUDs are also known to alter kappa-opioid receptors (KORs) and their endogenous ligands dynorphins (DYNs), and compounds targeting this signaling pathway have been proposed for treatment of SUDs (Walker B M et al. Alcohol. 2012 June; 46(4):359-70).

SUDs are also known to alter Corticotropin-Releasing Factor (CRF) receptor signaling, and CRF receptor (CRFR) antagonists have been proposed for treatment of SUDs (Lowery E G, Thiele T E. CNS Neurol Disord Drug Targets. 2010 March; 9(1):77-86).

Voltage- and calcium-gated ion channels are critical modulators of neuronal excitability, and modulators of ion channel function have also been proposed for treatment of SUDs. In particular, L-type voltage-dependent calcium channel (LVDCC) blockers (including the 1,4-dihydropyridine (DHP) derivatives israpidine, nimodipine, and nifedipine, and the phenylalkylamine verapamil) have been proposed for treatment of withdrawal symptoms in human addicts. N- and T-type calcium channels (NVDCC and TVDCC) blockers have also been proposed (Addolorato G et al. Neuropsychopharmacology. 2012 January; 37(1):163-77).

Lamotrigine, which inhibits sodium channel activity, has also been proposed for treatment of SUDs (Addolorato G et al. Neuropsychopharmacology. 2012 January; 37(1):163-77).

However, none of the above treatments is completely satisfactory and further treatment opportunities are needed. In particular, clinical results have not systematically confirmed preclinical results, or adverse effects limit the use of some compounds. For instance, CB1 receptor antagonist rimonabant is known to induce adverse effects such as severe depression and suicidal thoughts, which limits its potential use.

In addition, as illustrated above, many neurological signaling pathways are altered in SUDs, and many compounds modulating one of these pathways also modulate other signaling pathways, either directly (see the above examples of gabapentin and topiramate) or via metabolites generated in vivo having different activities. This makes understanding of crucial signaling pathways and of optimal active compounds extremely complicated.

3β-methoxy-pregna-5-ene-20-one (also referred to as 3β-methoxy-pregnenolone or 3β-methoxy-PREG) is a synthetic derivative of pregnenolone (3β-hydroxypregn-5-en-20-one), the natural precursor of steroid hormones, and in particular of neurosteroids. The 3β-methoxy function of 3β-methoxy-PREG prevents its conversion to its neuroactive metabolites.

It has been shown that 3β-methoxy-PREG is highly specific for its receptor MAP2. In particular, 3β-methoxy-PREG has no activity on progesterone receptor (see Example 11 of US20140228336A2 and Example 1 of the present description), and has also no androgenic, estrogenic, glucocorticoid and mineral corticoid activity (see Example 13 of US20140228336A2 and Example 2 of the present description). Moreover, 3β-methoxy-PREG has also been shown to have no significant affinity for many other receptors of the Central Nervous System (CNS), including muscarinic (cholinergic), histaminergic, noradrenergic, serotoninergic, dopaminergic, GABA, NMDA, cannabinoid, and opioid receptors (see Table 4 of US20140228336A2 and Example 3 of the present description). This compound is thus devoid of significant activity for most of signaling receptors known to be altered in SUDs, and for which modulation has been proposed as therapeutic strategy for treating SUDs.

SUMMARY OF THE INVENTION

However, in the context of the present invention, the inventors surprisingly found that 3β-methoxy-PREG is able to significantly and specifically reduce excessive alcohol drinking in a model of long time alcohol dependent rats, while showing no adverse effect.

The present invention thus relates to a compound of formula (I):

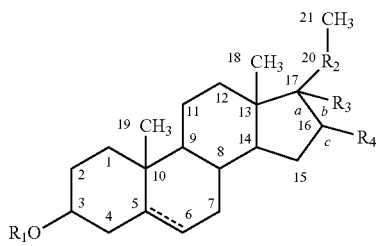

(I)

wherein:

each of ==== independently represents a single or a double bond;

$R_1$ represents a $C_1$-$C_4$ alkyl;

$R_2$ represents —CO—; —CH(OH)— or —CH(O—COCH$_3$)—; and $R_3$ represents H or CHCl$_2$ and $R_4$ represents H or CH$_3$, or $R_3$ and $R_4$ together represent

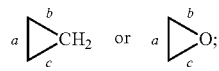

or a pharmaceutically acceptable salt thereof, for use in the treatment or relapse prevention of a substance use disorder.

The present invention also relates to a method for treating or preventing relapse of a substance use disorder in a subject in need thereof, comprising administering to said patient a therapeutically efficient amount of a compound of formula (I):

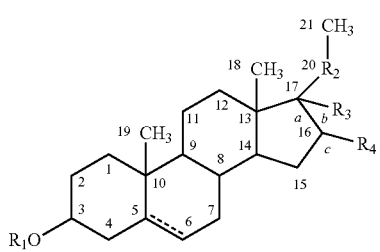

(I)

wherein:

each of ==== independently represents a single or a double bond;

$R_1$ represents a $C_1$-$C_4$ alkyl;

$R_2$ represents —CO—; —CH(OH)— or —CH(O—COCH$_3$)—; and $R_3$ represents H or CHCl$_2$ and $R_4$ represents H or CH$_3$, or $R_3$ and $R_4$ together represent

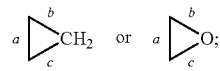

or a pharmaceutically acceptable salt thereof.

DETAILED DESCRIPTION OF THE INVENTION

Definitions

Figure 1:
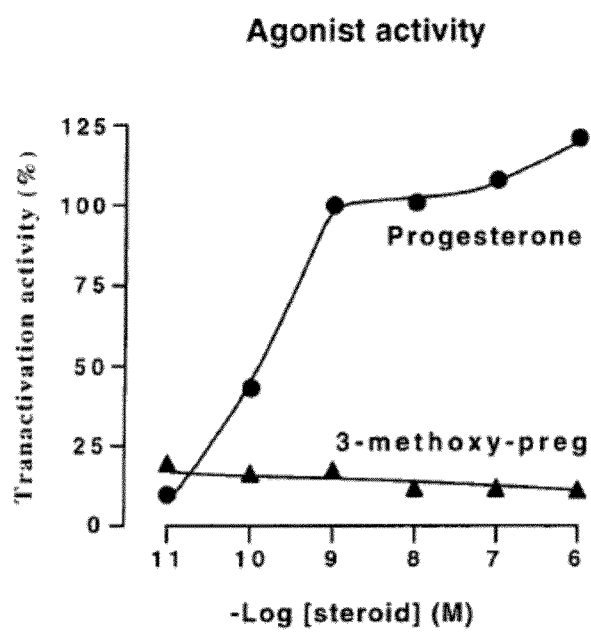
FIG. 1. Test of progesterone receptor agonist activity.

A "substance use disorder" or "SUD" is defined according to criteria of the 5th edition of the Diagnostic and Statistical Manual of Mental Disorders (DSM-5). In this respect, SUD is diagnosed if at least two of the following criteria are met within a 12-month period:

Impaired control criteria (1 to 4):
1. Substance is often taken in larger amounts or over a longer period than was intended.
2. There is a persistent desire or unsuccessful efforts to cut down or control substance use.
3. A great deal of time is spent in activities necessary to obtain substance, use substance, or recover from its effects.
4. Craving, or a strong desire or urge to use substance.

Social impairment criteria (5 to 7):
5. Recurrent substance use resulting in a failure to fulfill major role obligations at work, school, or home.
6. Continued substance use despite having persistent or recurrent social or interpersonal problems caused or exacerbated by the effects of substance.
7. Important social, occupational, or recreational activities are given up or reduced because of substance use.

Risky use of substance criteria (8 and 9):
8. Recurrent substance use in situations in which it is physically hazardous.
9. Substance use is continued despite knowledge of having a persistent or recurrent physical or psychological problem that is likely to have been caused or exacerbated by substance.

Pharmacological criteria (10 and 11):
10. Tolerance, as defined by either of the following:
    a) A need for markedly increased amounts of substance to achieve intoxication or desired effect
    b) A markedly diminished effect with continued use of the same amount of substance.
11. Withdrawal, as manifested by either of the following:
    a) The characteristic withdrawal syndrome for substance
    b) substance (or a closely related substance) is taken to relieve or avoid withdrawal symptoms.

SUD is considered as mild if 2 or 3 of the above criteria are met within said period of 12 months, moderate if 4 to 5 of the above criteria are met within said period of 12 months, and severe if 6 or more of the above criteria are met within said period of 12 months.

Substances that may lead to SUDs include: alcohol; cannabis; hallucinogens (including phencyclidine, ketamine, and LSD); opioids (including codeine, fentanyl, heroin, morphine, opium, methadone, oxycodone, and hydrocodone); sedative, hypnotic or anxiolytic medications (including barbiturates and benzodiazepines); stimulants (including nicotine, amphetamine, and methylphenidate); and inhalants (such as glue, shoe polish, toluene, spray paints, gasoline, and lighter fluid).

In particular, for "alcohol use disorder" or "AUD", AUD is diagnosed if at least two of the following criteria are met within a 12-month period:

Impaired control criteria (1 to 4):
1. Alcohol is often taken in larger amounts or over a longer period than was intended.
2. There is a persistent desire or unsuccessful efforts to cut down or control alcohol use.
3. A great deal of time is spent in activities necessary to obtain alcohol, use alcohol, or recover from its effects.
4. Craving, or a strong desire or urge to use alcohol.

Social impairment criteria (5 to 7):
5. Recurrent alcohol use resulting in a failure to fulfill major role obligations at work, school, or home.
6. Continued alcohol use despite having persistent or recurrent social or interpersonal problems caused or exacerbated by the effects of alcohol.
7. Important social, occupational, or recreational activities are given up or reduced because of alcohol use.

Risky use of alcohol criteria (8 and 9):
8. Recurrent alcohol use in situations in which it is physically hazardous.
9. Alcohol use is continued despite knowledge of having a persistent or recurrent physical or psychological problem that is likely to have been caused or exacerbated by alcohol.

Pharmacological criteria (10 and 11):
10. Tolerance, as defined by either of the following:
    a) A need for markedly increased amounts of alcohol to achieve intoxication or desired effect
    b) A markedly diminished effect with continued use of the same amount of alcohol.
11. Withdrawal, as manifested by either of the following:
    a) The characteristic withdrawal syndrome for alcohol
    b) Alcohol (or a closely related substance, such as a benzodiazepine) is taken to relieve or avoid withdrawal symptoms.

AUD is considered as mild if 2 or 3 of the above criteria are met within said period of 12 months, moderate if 4 to 5 of the above criteria are met within said period of 12 months, and severe if 6 or more of the above criteria are met within said period of 12 months.

By "treatment" or "treating" is meant an improvement of clinical or biological criteria in the subject. For instance, "treatment" or "treating" may correspond to a decrease in the number or intensity of criteria 1 to 11 defined above for substance use disorders. By "prevention" or "preventing" is meant the fact to prevent or delay the onset or reduce the intensity of clinical or biological criteria associated to the substance use disorder. More precisely, in the context of "relapse prevention", it is referred to the fact to the fact to prevent or delay substance use disorder relapse or to reduce the intensity of substance use disorder relapse. In the case of reducing the intensity of substance use disorder relapse, the reduction may correspond to the presence of a decreased number of the 11 above defined criteria or to the presence of the same criteria as before but with reduced intensity.

A "therapeutically effective amount" corresponds to an amount necessary to impart therapeutic or a preventive benefit to a subject, as defined above.

For the purpose of the present invention, the term "$C_1$-$C_4$ alkyl" is intended to mean any linear or branched saturated hydrocarbon radical having from one to four carbon atoms. Examples of $C_1$-$C_4$ alkyl groups include a methyl ($CH_3$) or an ethyl ($C_2H_6$) group. "Pharmaceutically acceptable salts" refer to salts that are suitable for use in contact with the tissues of humans and animals without undue toxicity, irritation, allergic response, and the like. Examples of suitable salts include salts of alkali metals such as potassium, sodium, lithium, salts of alkaline earth metals such as calcium, magnesium and acid addition salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, hemisuccinic acid, tartaric acid, methane-sulfonic acid, p-toluene-sulphonic acid, trifluoro acetic acid and the like.

Compounds for Use in the Treatment of SUDs

The present invention relates to a compound of formula (I):

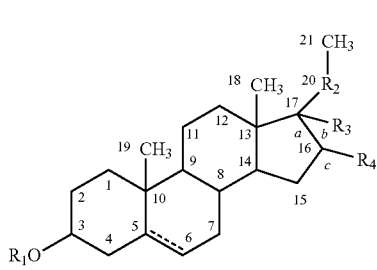

(I)

wherein:
each of ===== independently represents a single or a double bond;
$R_1$ represents a $C_1$-$C_4$ alkyl;
$R_2$ represents —CO—; —CH(OH)— or —CH(O—COCH$_3$)—; and
$R_3$ represents H or CHCl$_2$ and $R_4$ represents H or CH$_3$, or $R_3$ and $R_4$ together represent

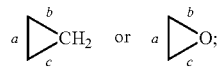

or a pharmaceutically acceptable salt thereof,
for use in the treatment or relapse prevention of a substance use disorder.

The present invention also relates to a method for treating or preventing relapse of a substance use disorder in a subject in need thereof, comprising administering to said patient a therapeutically efficient amount of a compound of formula (I):

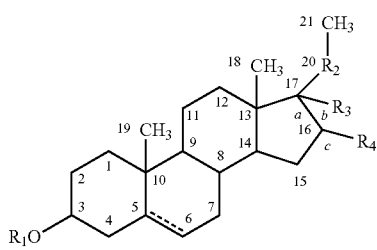

(I)

wherein:
each of ===== independently represents a single or a double bond;
$R_1$ represents a $C_1$-$C_4$ alkyl;
$R_2$ represents —CO—; —CH(OH)— or —CH(O—COCH$_3$)—; and
$R_3$ represents H or CHCl$_2$ and $R_4$ represents H or CH$_3$, or $R_3$ and $R_4$ together represent

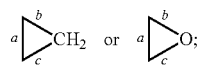

or a pharmaceutically acceptable salt thereof.

Stereochemistry may be important for activity of the compound of formula (I). As a result, in the above therapeutic uses, the compound is preferably of a compound of formula (Ib), and even more preferably a compound of formula (Ic):

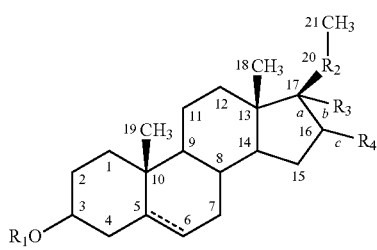

(Ib)

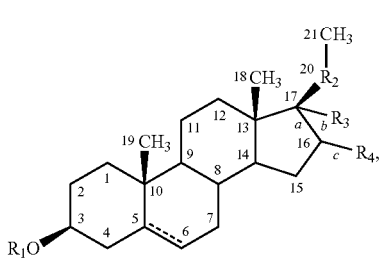

(Ic)

wherein:
each of ===== independently represents a single or a double bond;
$R_1$ represents a $C_1$-$C_4$ alkyl;
$R_2$ represents —CO—; —CH(OH)— or —CH(O—COCH$_3$)—; and
$R_3$ represents H or CHCl$_2$ and $R_4$ represents H or CH$_3$, or $R_3$ and $R_4$ together represent

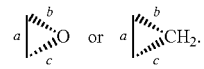

Preferably, in the above therapeutic uses, the compound is of formula (II):

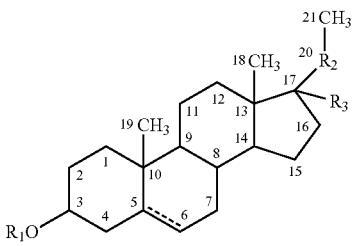

(II)

wherein:
===== represents a single or a double bond;
$R_1$ represents a $C_1$-$C_4$ alkyl;
$R_2$ represents —CO— or —CH(OH)—; and
$R_3$ represents H or CHCl$_2$.

In formula (II) also, stereochemistry may be important for activity of the compound. As a result, in the above therapeutic uses, the compound is preferably of a compound of formula (IIb), and even more preferably a compound of formula (IIc):

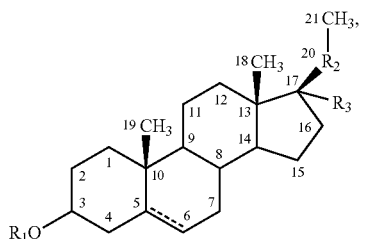

(IIb)

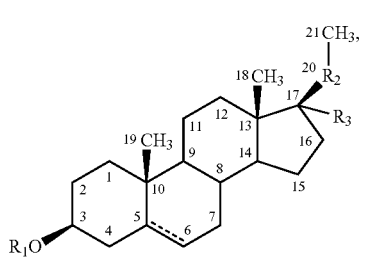

(IIc)

wherein ====, $R_1$, $R_2$, and $R_3$ are as defined above for formula (II).

In a preferred embodiment of anyone of formulas (I), (Ib), (Ic), (II), (IIb), and (IIc) above, $R_1$ is $CH_3$.

Alternatively or in combination, in anyone of formulas (I), (Ib), (Ic), (II), (IIb), and (IIc) above, ==== is preferably a double bond.

Alternatively or in combination, in anyone of formulas (I), (Ib), (Ic), (II), (IIb), and (IIc) above, $R_2$ is preferably —CO—.

Alternatively or in combination, in anyone of formulas (I), (Ib), (Ic), (II), (IIb), and (IIc) above, $R_3$ represents H.

It should be noted that any preferred bond/group for any of the substituents may be combined with any other preferred bond/group for another of the substituents.

Preferred compounds for the above therapeutic uses are those described in Table 1 below, or any pharmaceutically acceptable salt thereof:

TABLE 1

| Preferred compounds for use in the invention | |
| --- | --- |
| Compound | Formula |
| 3-methoxy-pregna-5-ene-20-one | (structure) |

TABLE 1-continued

| Preferred compounds for use in the invention | |
| --- | --- |
| Compound | Formula |
| 3-methoxy-pregna-5-ene-20-ol | (structure) |
| 3-methoxy-pregna-5-ene-20-one-17-dichloromethyl | (structure) |
| 3-methoxy-5-pregnane-20-one | (structure) |
| 3-methoxy-5-pregnane-20-ol | (structure) |

A particularly preferred compound is 3-methoxy-pregna-5-ene-20-one (3-methoxy-PREG), of formula:

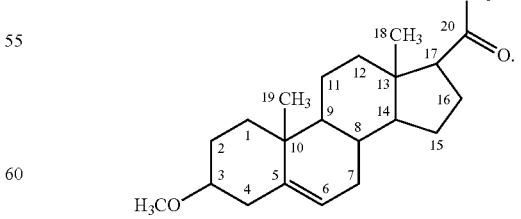

For compounds also, stereochemistry may be important for activity of the compound. As a result, in the above therapeutic uses, the compound is preferably selected from those described in Table 2 below, or any pharmaceutically acceptable salt thereof:

TABLE 2

| Preferred compounds for use in the invention | |
|---|---|
| Compound | Formula |
| 3β-methoxy-pregna-5-ene-20-one | *(structure)* |
| 3β-methoxy-pregna-5-ene-20β-ol | *(structure)* |
| 3β-methoxy-pregna-5-ene-20α-ol | *(structure)* |
| 3β-methoxy-pregna-5-ene-20-one-17α-dichloromethyl | *(structure)* |
| 3β-methoxy-5α-pregnane-20-one | *(structure)* |
| 3β-methoxy-5α-pregnane-20β-ol | *(structure)* |

TABLE 2-continued

Preferred compounds for use in the invention

| Compound | Formula |
|---|---|
| 3β-methoxy-5α-pregnane-20α-ol | 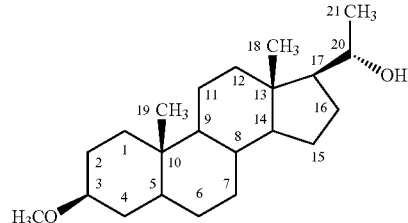 |

A particularly preferred compound is 3β-methoxy-pregna-5-ene-20-one (3β-methoxy-PREG), of formula:

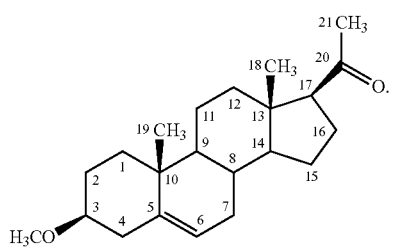

Preparation of the Compounds

The above defined compounds or pharmaceutically acceptable salts thereof may be prepared easily using conventional synthesis chemistry, starting from corresponding commercially available compounds with an OH group in position C3.

In particular, 3β-methoxy-PREG may be prepared from pregnenolone by addition of p-toluenesulfonyl chloride in pyridine, stirring of the mixture, addition of distilled water, cooling of the reaction to 0° C., filtration and drying under vacuum to yield pregnenolone tosylate. Pregnenolone tosylate is then refluxed with methanol for 4 hours. After cooling and evaporation of the solvent, the crude reaction product is washed in 10% sodium bicarbonate solution. After drying the organic phase over $Na_2SO_4$, it is evaporated dry under reduced pressure to yield 3β-methoxy-PREG. A precise protocol is disclosed in Example 1 of WO2004067010A1. 3β-methoxy-PREG is also commercially available, for instance from Steraloids Inc (Newport, R.I., USA). Similar methods may be used for preparation of other non-bioconvertible $C_3$-substituted pregnenolone derivatives useful in the context of the present invention, starting from corresponding commercially available compounds with an OH group in position C3.

Administration of the Compounds

The above defined compounds or pharmaceutically acceptable salts thereof, and in particular 3β-methoxy-PREG or pharmaceutically acceptable salts thereof, may be administered to any subject suffering from a substance use disorder, in particular to any human subject suffering from a substance use disorder.

The above defined compounds or pharmaceutically acceptable salts thereof, and in particular 3β-methoxy-PREG or pharmaceutically acceptable salts thereof, may be administered to a (preferably human) subject suffering from a substance use disorder via any suitable administration route, including oral, intravenous, transdermal, subcutaneous, intranasal, topical, sublingual, and rectal routes. Preferred administrations routes include oral, subcutaneous, and intranasal routes.

Depending on the selected route of administration, those skilled in the art will know how to formulate the above defined compounds or pharmaceutically acceptable salts thereof in order to optimize in vivo delivery and bioavailability. In particular, the above defined compounds or pharmaceutically acceptable salts thereof, and in particular 3β-methoxy-PREG or pharmaceutically acceptable salts thereof, may be formulated with suitable pharmaceutically acceptable carriers, excipients, vehicles, preservatives, solubilizing agents, stabilizers, wetting agents, emulsifiers, sweeteners, dyes, flavoring, salts intended to modify osmotic pressure, buffers, taste correctors, and antioxidants. These compounds are well-known to those skilled in the art. Details on these chemicals can be found in the latest edition of Remington's Pharmaceutical Sciences (Maack Publishing Co., Easton, Pa.). The selection of the optimal delivery formulation will be selected by those skilled in the art depending on the selected administration route.

Suitable unit dose administration formulations for oral administration notably include tablets, coated tablets, pills, capsules and soft gelatin capsules, oral powders, granules, solutions and suspensions.

When a solid composition in tablet form is prepared, the principal active ingredient may be mixed with a pharmaceutical vehicle, such as gelatin, starch, lactose, stearic acid or magnesium stearate, talc, gum arabic or analogues. The tablets may be coated with saccharose or other suitable materials or even be treated so as to have a prolonged or delayed activity and to release continuously a predetermined quantity of the active ingredient.

A capsule preparation may be obtained by mixing the active ingredient with a thinner and pouring the mixture obtained into soft or hard capsules, with excipients such as vegetable oils, waxes, fats, semi-solid or liquid polyols, etc.

A preparation in syrup or elixir form can contain the active ingredient together with a sweetener, an antiseptic, as well as an agent giving taste and a suitable dye. Excipients may be used, such as water, polyols, saccharose, invert sugar, glucose, etc.

Powders or water-dispersible granules may contain the active ingredient in a mixture with dispersing agents, wetting agents, and suspending agents, together with taste correctors and sweeteners.

For intravenous or intranasal administration, aqueous suspensions, isotonic saline solutions, or sterile, injectable solutions that contain pharmacologically compatible dispersing agents and/or wetting agents may be used. As an excipient, water, alcohols, polyols, glycerol, vegetable oils, etc., may be used.

For subcutaneous administration, any suitable pharmaceutically acceptable vehicle may be used. In particular, a pharmaceutically acceptable oil vehicle, such as sesame oil, may be used.

For topical administration, compositions may be presented in the form of a gel, a paste, an ointment, a cream, a lotion, an aqueous or aqueous-alcohol liquid suspension, an oily solution, a dispersion of the lotion or serum type, an anhydrous or lipophilic gel, an emulsion with a liquid or semi-solid milk-type consistency obtained by dispersing a fatty phase in an aqueous phase or vice versa, suspensions or emulsions of a soft or semi-solid cream- or gel-type consistency, or alternatively microemulsions, microcapsules, microparticles, or vesicular dispersions of the ionic and/or nonionic type. These compositions are prepared according to standard methods. Moreover, a surfactant can be included in the composition in order to enable deeper penetration of the above defined compounds or pharmaceutically acceptable salts thereof, and in particular 3β-methoxy-PREG or pharmaceutically acceptable salts thereof. An agent enabling an increased penetration may be selected, for example, from mineral oil, ethanol, triacetin, glycerin and propylene glycol; cohesion agents are selected, for example, from the group comprising polyisobutylene, polyvinyl acetate, polyvinyl alcohol, and thickening agents.

For rectal administration, suppositories, which are prepared with binders that melt at rectal temperatures, for example cocoa butter or semi-solid or liquid polyols such as polyethylene glycols, waxes, natural or hydrogenated oils, fats, etc., can be used.

The above defined compounds or pharmaceutically acceptable salts thereof, and in particular 3β-methoxy-PREG or pharmaceutically acceptable salts thereof, may be administered to a (preferably human) subject suffering from a substance use disorder at any dose suitable for obtaining a therapeutic effect. In particular, a suitable dose for humans may be in the range of 50 to 2000 mg/day, in particular in the range of 50 to 1750 mg/day, in the range of 50 to 1500 mg/day, in the range of 50 to 1250 mg/day, in the range of 50 to 1000 mg/day, in the range of 50 to 750 mg/day, in the range of 50 to 500 mg/day, in the range of 100 to 2000 mg/day, in particular in the range of 100 to 1750 mg/day, in the range of 100 to 1500 mg/day, in the range of 100 to 1250 mg/day, in the range of 100 to 1000 mg/day, in the range of 100 to 750 mg/day, in the range of 100 to 500 mg/day, in the range of 250 to 2000 mg/day, in particular in the range of 250 to 1750 mg/day, in the range of 250 to 1500 mg/day, in the range of 250 to 1250 mg/day, in the range of 250 to 1000 mg/day, in the range of 250 to 750 mg/day, in the range of 250 to 500 mg/day, in the range of 500 to 2000 mg/day, in the range of 500 to 1750 mg/day, in the range of 500 to 1500 mg/day, in the range of 500 to 1250 mg/day, in the range of 500 to 1000 mg/day, or in the range of 500 to 750 mg/day.

The administered dose may vary depending on the subject age, body surface area or body weight, or on the administration route and associated bioavailability. Such dose adaptation is well known to those skilled in the art.

SUDs to be Treated

The above defined compounds or pharmaceutically acceptable salts thereof, and in particular 3β-methoxy-PREG or pharmaceutically acceptable salts thereof, may be used for treating any SUD. Indeed, most SUDs share at least some common etiologies, alterations of neurological signaling pathways and behaviors (Vanyukov M M, et al. Neurosci Biobehav Rev. 2003 October; 27(6):507-15; Koob G F, Volkow N D. Neuropsychopharmacology. 2010 January; 35(1):217-38; Koob G F, Le Moal M. Philos Trans R Soc Lond B Biol Sci. 2008 Oct. 12; 363(1507):3113-23) and results obtained in models of alcohol use disorder may thus reasonably be extended to other substance use disorders. In particular, all SUD share:

Common liabilities (Vanyukov M M, et al. Neurosci Biobehav Rev. 2003 October; 27(6):507-15), Common mechanisms of (Koob G F, Volkow N D. Neuropsychopharmacology. 2010 January; 35(1):217-38; Koob G F, Le Moat M. Philos Trans R Soc Lond B Biol Sci. 2008 Oct. 12; 363(1507):3113-23):
  early neuroadaptation, with increased excitability of the mesolimbic dopamine system reflected in long-term potentiation dependent on changes in glutamate activity
  common response of elevated adrenocorticotropic hormone, corticosterone and amygdala CRF during acute withdrawal Common behaviors of withdrawal/negative affect and preoccupation/anticipation (Koob G F, Volkow N D. Neuropsychopharmacology. 2010 January; 35(1):217-38; Koob G F, Le Moat M. Philos Trans R Soc Lond B Biol Sci. 2008 Oct. 12; 363(1507):3113-23).

The above defined compounds or pharmaceutically acceptable salts thereof, and in particular 3β-methoxy-PREG or pharmaceutically acceptable salts thereof, may thus be used for treating alcohol use disorder; cannabis use disorder; hallucinogens (including phencyclidine, ketamine, and LSD) use disorders; opioids (including codeine, fentanyl, heroin, morphine, opium, methadone, oxycodone, and hydrocodone) use disorders; sedative, hypnotic or anxiolytic medications (including barbiturates and benzodiazepines) use disorders; stimulants (including nicotine, amphetamine, and methylphenidate) use disorders; and inhalants (such as glue, shoe polish, toluene, spray paints, gasoline, and lighter fluid) use disorders.

In a preferred embodiment, the above defined compounds or pharmaceutically acceptable salts thereof, and in particular 3β-methoxy-PREG or pharmaceutically acceptable salts thereof, are for use in the treatment of alcohol use disorder.

The following examples merely intend to illustrate the present invention.

EXAMPLES

Example 1. Activity of 3β-Methoxy-Pregnenolone on Progesterone Receptor

The capacity of 3β-methoxy-pregnenolone to display progesterone activity, and thus to be considered as a progestin, was tested by assaying the activity of 3-methoxy-pregnenolone on progesterone receptor.

Indeed, progesterone is an agonist of progesterone receptor, as are all progestins. In contrast, compounds able to inhibit progesterone activity on its receptor are called progesterone receptor antagonists.

Methods

The main experimental setting used is the following: HEK293T cells were transiently transfected, using calcium phosphate precipitation technology, with expression vectors pSG5hPR (which permits expression of human progesterone receptor (PR)), pFC31-luc (contains the luciferase gene under the control of the MMTV promoter, which is in turn activated by binding of a progestin to progesterone receptor) and pcbetagal (which permits expression of betagalactosidase), and cultured during 24 hours with increasing amounts of various compositions:

1. Test of progesterone receptor agonist activity: transfected cells were cultured with increasing amounts of progesterone or 3-methoxy-pregnenolone
   With this setting, a compound with progesterone receptor agonist activity permits a transactivation activity resulting in the expression of luciferase (since the binding of a progestin to PR results in activation of the MMTV promoter, which directs the expression of luciferase).

In contrast, a compound without progesterone receptor agonist activity does not permit a transactivation activity and luciferase is not expressed (since PR is not activated and thus does not activate the MMTV promoter);
2. Test of progesterone receptor agonist activity: transfected cells were cultured with progesterone (1 nM) and increasing amounts of RU486 (a well-known progesterone receptor antagonist) or 3-methoxy-pregnenolone.

With this setting, a compound with progesterone receptor antagonist activity competes with progesterone for the occupation of progesterone receptor and results in a progressive loss of transactivation activity when the amount of this compound is increased compared to progesterone.

Results

The results obtained with experimental setting 1 (test of progesterone receptor agonist activity) are displayed in FIG. 1.

FIG. 1 clearly shows that, contrary to progesterone, which permits a transactivation activity leading to the expression of luciferase, 3-methoxy-pregnenolone does not permit such a transactivation activity, even at the highest tested concentrations, thus demonstrating that 3β-methoxy-pregnenolone does not have progesterone receptor agonist activity, and cannot thus be considered as a progestin.

Figure 2:
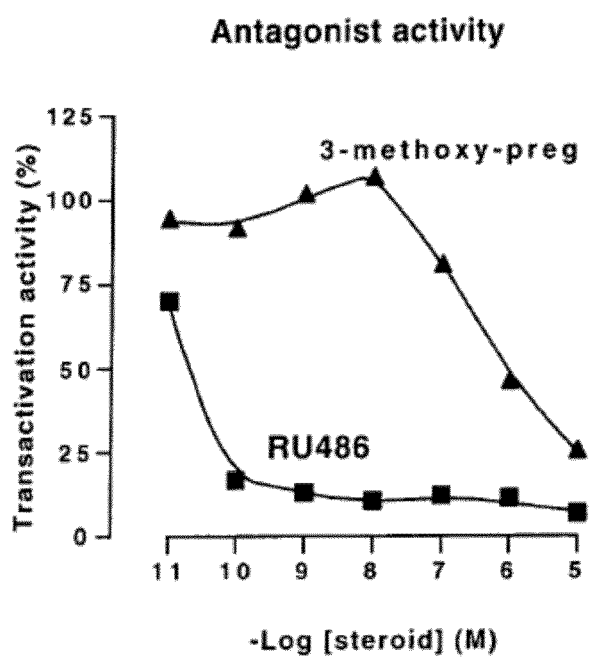
FIG. 2. Test of progesterone receptor antagonist activity.

The results obtained with experimental setting 2 (test of progesterone receptor antagonist activity) are displayed in FIG. 2.

These results unambiguously show that even if 3β-methoxy-pregnenolone does not have the very high antagonist activity of RU486, it is a weak progesterone receptor antagonist.

Example 2. 3β-Methoxy-PREG has No Androgenic, Estrogenic, Glucocorticoid and Mineral Corticoid Activity Binding affinity of 3β-methoxy-PREG (MAP4343) for receptors of steroid hormones was evaluated using radioligand binding assays.

MAP4343 (10 μM) was ineffective (<25% inhibition) in displacing specific radioligands from the following binding sites: Mineralocorticoid Receptor (MR), Androgen Receptor (AR), Estrogen Receptors (ERα and ERβ) and Glucocorticoid Receptor (GR). The results are summarized below in Table 3 below.

TABLE 3

Affinity of MAP4343 (10 μM) for steroid hormones receptors measured by radioligand binding assays. Biochemical assay results are presented as the percent inhibition of specific binding (significant responses: ≥50% inhibition). None of the results met significance criteria at concentrations used.

| Target | Ligand | Source | % inhibition* |
|---|---|---|---|
| MR | 4.5 nM [$^3$H] D-Aldosterone | Wistar Rat kidney | 25 |
| AR | 1.5 nM [$^3$H] Mibolerone | Rat recombinant E. coli | 18 |
| ER☐ | 0.5 nM [$^3$H] Estradiol | Human recombinant Sf9 cells | −8 |
| ER☐ | 0.5 nM [$^3$H] Estradiol | Human recombinant Sf9 cells | 16 |
| GR | 3 nM [$^3$H] Dexamethasone | Human HeLa S3 cells | 21 |

*Negative values correspond to stimulation of binding or enzyme activity

Example 3. 3β-Methoxy-PREG has No Significant Affinity for Receptors of the Central Nervous System MAP4343 has been screened for in vitro affinity to 80 different CNS neurotransmitters receptors using various validated binding assays.

The results show that MAP4343 has no significant affinity for any tested receptor including the ones traditionally associated with side effects or abuse liability. Results are summarized in following Table 4.

TABLE 4

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| Muscarinic (Cholinergic) | $M_1$ | [$^3$H] pirenzepine | Human recombinant (CHO cells) | −3 |
| | $M_2$ | [$^3$H] AF-DX 384 | Human recombinant (CHO cells) | 20 |
| | $M_3$ | [$^3$H] 4-DAMP | Human recombinant (CHO cells) | 3 |
| | $M_4$ | [$^3$H] 4-DAMP | Human recombinant (CHO cells) | 20 |
| | $M_5$ | [$^3$H] 4-DAMP | Human recombinant (CHO cells) | 12 |
| Histaminergic | $H_1$ | [$^3$H] pyrilamine | Human recombinant (HEK-293 cells) | 9 |
| | $H_2$ | [$^{125}$I] APT | Human recombinant (CHO cells) | −21 |
| Noradrenergic | $\alpha_1$ | [$^3$H] prazosin | rat cerebral cortex | 4 |
| | $\alpha_2$ | [$^3$H] RX 821002 | rat cerebral cortex | 7 |
| | $\beta_1$ | [$^3$H] (−) CGP 12177 | Human recombinant (HEK-293 cells) | 1 |
| | $\beta_2$ | [$^3$H] (−) CGP 12178 | Human recombinant (CHO cells) | −4 |
| | Transporter | [$^3$H] nisoxetine | Human recombinant (CHO cells) | 3 |
| Serotoninergic | 5-$HT_{1A}$ | [$^3$H] 8-OH-DPAT | Human recombinant (HEK-293 cells) | 2 |
| | 5-$HT_{1B}$ | [$^{125}$I] CYP + (−) propranolol | rat cerebral cortex | 4 |
| | 5-$HT_{2A}$ | [$^3$H] ketanserin | Human recombinant (HEK-293 cells) | 1 |
| | 5-$HT_{2B}$ | [$^{125}$I] (±) DOI | Human recombinant (CHO cells) | −4 |

TABLE 4-continued

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| | $5\text{-HT}_{2C}$ | [$^3$H] mesulergine | Human recombinant (CHO cells) | 7 |
| | $5\text{-HT}_3$ | [$^3$H] BRL 43694 | Human recombinant (CHO cells) | 10 |
| | $5\text{-HT}_{5A}$ | [$^3$H] LSD | Human recombinant (CHO cells) | −5 |
| | $5\text{-HT}_6$ | [$^3$H] LSD | Human recombinant (CHO cells) | 12 |
| | $5\text{-HT}_7$ | [$^3$H] LSD | Human recombinant (CHO cells) | −11 |
| | Transporter | [$^3$H] imipramine | Human recombinant (CHO cells) | 3 |
| Dopaminergic | $D_1$ | [$^3$H] SCH 23390 | Human recombinant (CHO cells) | 2 |
| | $D_{2S}$ | [$^3$H] spiperone | Human recombinant (HEK-293 cells) | 6 |
| | $D_3$ | [$^3$H] spiperone | Human recombinant (CHO cells) | 8 |
| | $D_{4.4}$ | [$^3$H] spiperone | Human recombinant (CHO cells) | 6 |
| | $D_5$ | [$^3$H] SCH 23390 | Human recombinant (GH4 cells) | −7 |
| | Transporter | [$^3$H] BTCP | Human recombinant (CHO cells) | |
| GABA | (non-selective) | [$^3$H] GABA | rat cerebral cortex | 2 |
| NMDA | PCP site | [$^3$H] TCP | rat cerebral cortex | −10 |
| Cannabinoid | $CB_1$ | [$^3$H] CP 55940 | Human recombinant (CHO cells) | 12 |
| Oppioid | $\delta_2$ | [$^3$H] DADLE | Human recombinant (CHO cells) | −3 |
| | κ | [$^3$H] U 69593 | rat recombinant (CHO cells) | 19 |
| | μ | [$^3$H] DAMGO | Human recombinant (HEK-293 cells) | 0 |

Example 4: Effect of Chronic 3β-Methoxy-PREG on Alcohol Self-Administration in Ethanol Dependent and Non-Dependent Animals Alcohol self-administration in ethanol dependent and non-dependent animals is a well-known and well-characterized animal model for analysis of alcoholism behaviors (Roberts et al. 1999, 2000; Rimondini et al. 2002; O'Dell et al. 2004; Richardson et al. 2008; Gilpin et al. 2009). Numerous studies have demonstrated that this model has robust predictive validity for alcohol addiction (Heilig and Koob 2007; Koob et al. 2009) This model has been used to test the effect of chronic 3β-methoxy-PREG administration in a model of alcoholism.

Materials and Methods

Subjects

Adult male Wistar rats (Charles River, Raleigh, N.C.), weighing 225-275 g at the beginning of the experiments, were housed in groups of 2-3 per cage in a temperature-controlled (22° C.) vivarium on a 12 h/12 h light/dark cycle (lights on at 8:00 PM) with ad libitum access to food and water. All behavioral tests were conducted during the dark phase of the light/dark cycle. All procedures adhered to the National Institutes of Health Guide for the Care and Use of Laboratory Animals and were approved by the Institutional Animal Care and Use Committee of The Scripps Research Institute.

Operant Self-Administration

Self-administration sessions were conducted in standard operant conditioning chambers (Med Associates, St. Albans, Vt.). Animals were first trained to self-administer 10% (w/v) ethanol and water solutions until a stable response was maintained. The rats were subjected to an overnight session in the operant chambers with access to one lever (right lever) that delivered water (FR1). Food was available ad libitum during this training. After 1 day off, the rats were subjected to a 2 h session (FR1) for 1 day and a 1 h session (FR1) the next day, with one lever delivering alcohol (right lever). All of the subsequent sessions lasted 30 min, and two levers were available (left lever: water; right lever: alcohol) until stable levels of intake were reached. Upon completion of this procedure, the animals were allowed to self-administer a 10% (w/v) alcohol solution and water on an FR1 schedule of reinforcement (i.e., each operant response was reinforced with 0.1 ml of the solution).

Alcohol Vapor Chambers

Once a stable baseline of alcohol self-administration was reached, the rats were made dependent by chronic, intermittent exposure to alcohol vapors. They underwent cycles of 14 h on (blood alcohol levels during vapor exposure ranged between 150 and 250 mg %) and 10 h off, during which behavioral testing for acute withdrawal occurred (i.e., 6-8 h after vapor was turned off when brain and blood alcohol levels are negligible). In this model, rats exhibit somatic withdrawal signs and negative emotional symptoms reflected by anxiety-like responses and elevated brain reward thresholds. Nondependent rats were not exposed to alcohol vapor.

Operant Self-Administration During Alcohol Vapor Exposure

Behavioral testing occurred 3 times per week. The rats were tested for alcohol (and water) self-administration on an FR1 schedule of reinforcement for 30 min sessions. Operant self-administration on an FR1 schedule requires minimal effort by the animal to obtain the reinforcement and herein was considered a measure of intake.

Drugs

Alcohol drinking solution 10% (w/v) was prepared by dilution of ethanol 95% (w/v) in water. 3β-methoxy-PREG (referred to as "MAP4343" in Example 1) was dissolved in sesame oil and injected sub-cutaneously at the dose of 10 mg/kg 24 hours before each test session.

Blood Samples

Blood samples were obtained before and after completion of the treatment with MAP4343 using retro-orbital sampling. Blood, serum and plasma were collected and analyzed using standard procedures to evaluate blood count panel, blood urea nitrogen, cholesterol, creatinine, T3, T4 and protein electrophoresis.

Statistical Analysis

Figure 3:
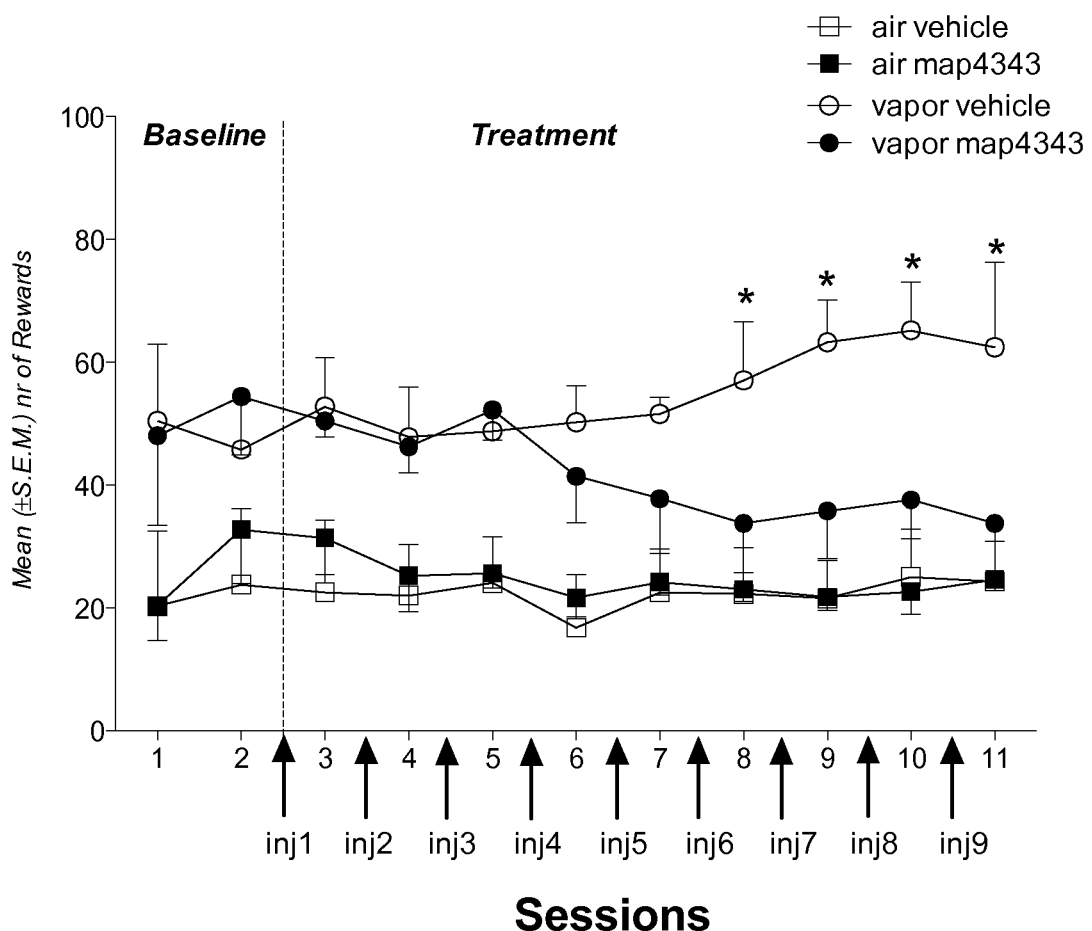
FIG. 3. Effect of chronic MAP4343 (10 mg/kg) on alcohol self-administration in dependent (vapor) and non-dependent (air) animals. Values represent the mean (±S.E.M) number of alcohol reinforced responses. *: significant (p<0.05) difference between vapor vehicle and vapor MAP4343.
Figure 4:
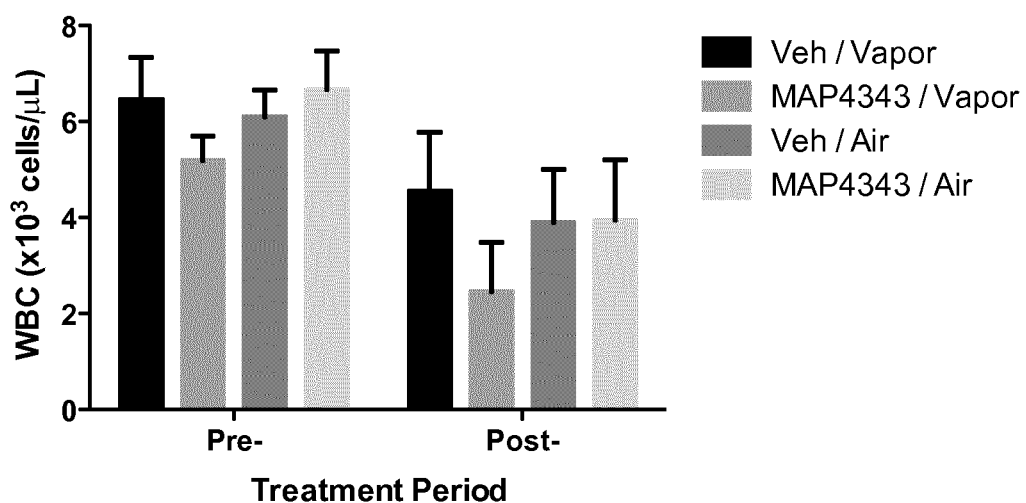
FIG. 4. White blood cells (WBC) counts (×10$^3$ cells/μL) in dependent (Vapor) and non-dependent (Air) rats before (pre-treatment) and after (post-treatment) treatment with vehicle (Veh) or MAP4343.
Figure 5:
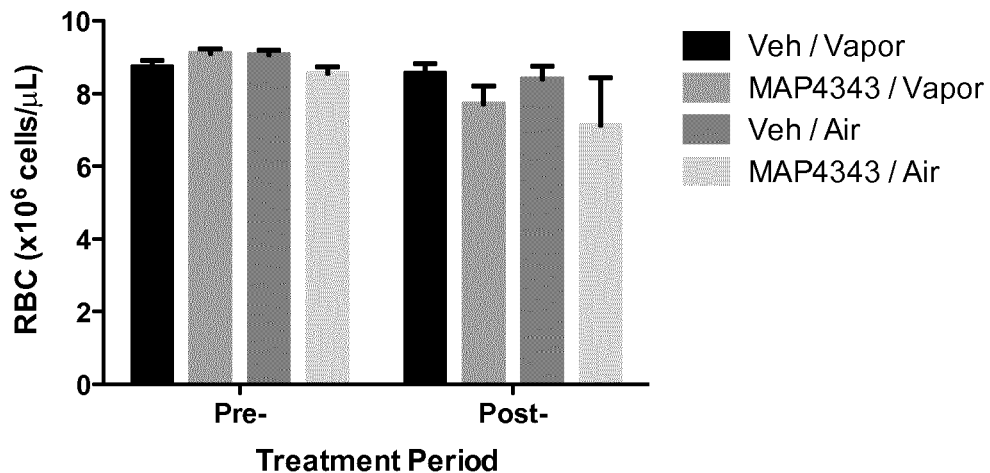
FIG. 5. Red blood cells (RBC) counts (×10$^6$ cells/μL) in dependent (Vapor) and non-dependent (Air) rats before (pre-treatment) and after (post-treatment) treatment with vehicle (Veh) or MAP4343.
Figure 6:
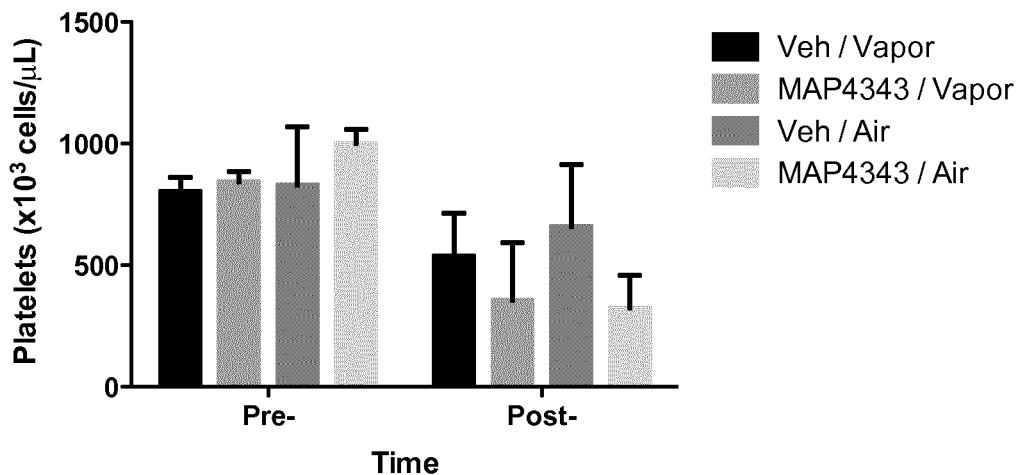
FIG. 6. Platelets counts (×10$^3$ cells/μL) in dependent (Vapor) and non-dependent (Air) rats before (pre-treatment) and after (post-treatment) treatment with vehicle (Veh) or MAP4343.
Figure 7:
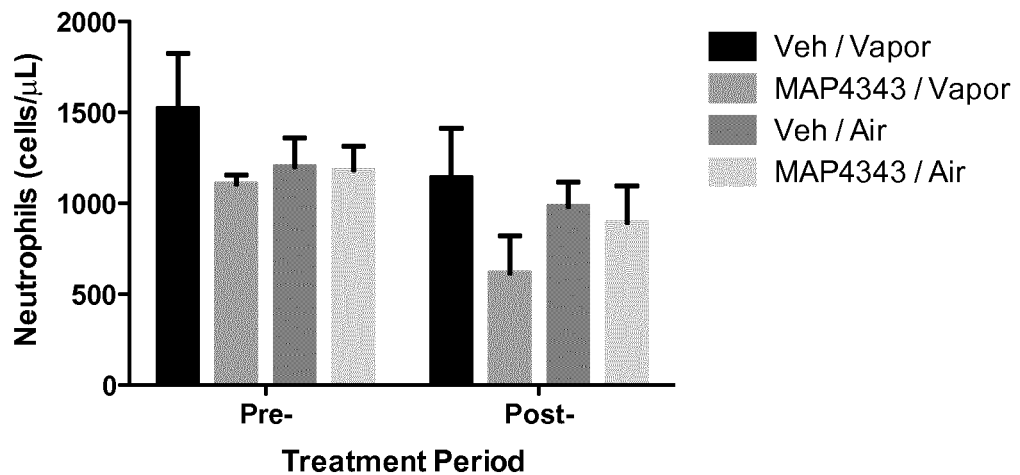
FIG. 7. Neutrophils counts in dependent (Vapor) and non-dependent (Air) rats before (pre-treatment) and after (post-treatment) treatment with vehicle (Veh) or MAP4343.
Figure 8:
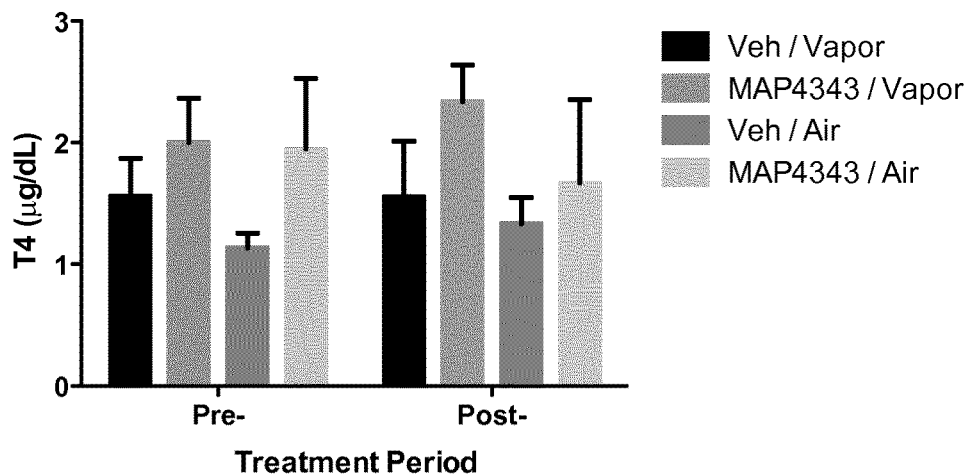
FIG. 8. T4 level (μg/dL) in dependent (Vapor) and non-dependent (Air) rats before (pre-treatment) and after (post-treatment) treatment with vehicle (Veh) or MAP4343.
Figure 9:
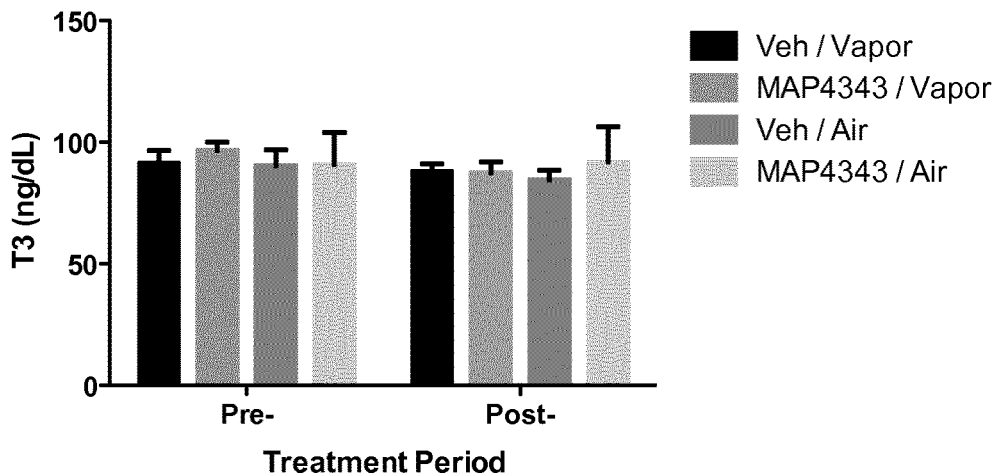
FIG. 9. T3 level (ng/dL) in dependent (Vapor) and non-dependent (Air) rats before (pre-treatment) and after (post-treatment) treatment with vehicle (Veh) or MAP4343.
Figure 10:
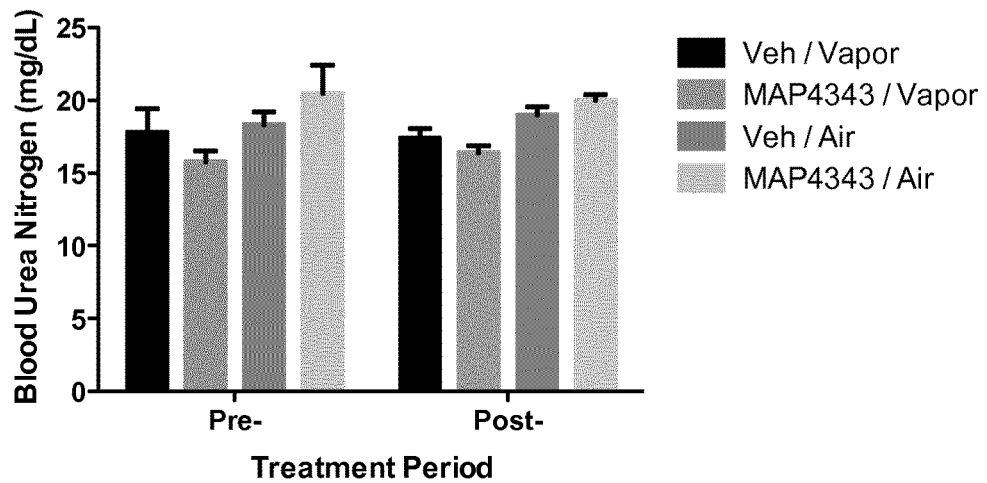
FIG. 10. Blood urea nitrogen level (mg/dL) in dependent (Vapor) and non-dependent (Air) rats before (pre-treatment) and after (post-treatment) treatment with vehicle (Veh) or MAP4343.
Figure 11:
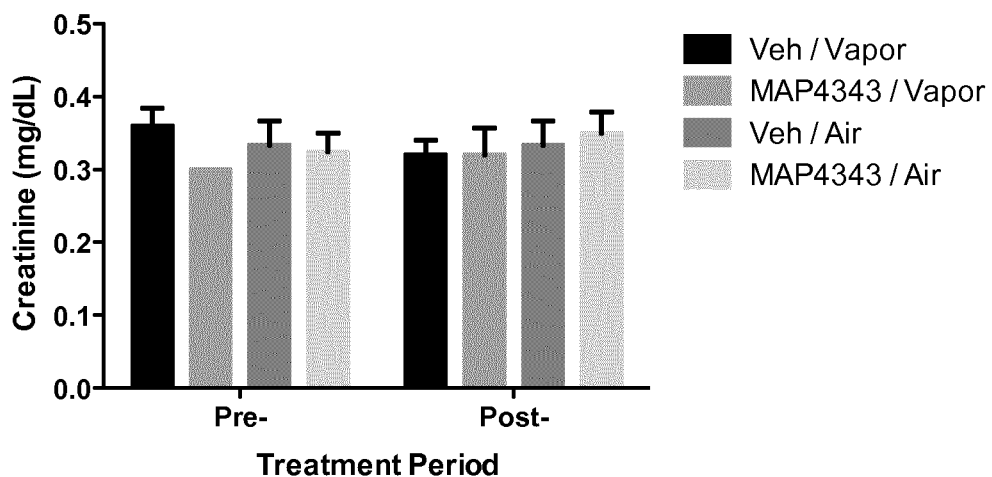
FIG. 11. Creatinine level (mg/dL) in dependent (Vapor) and non-dependent (Air) rats before (pre-treatment) and after (post-treatment) treatment with vehicle (Veh) or MAP4343.
Figure 12:
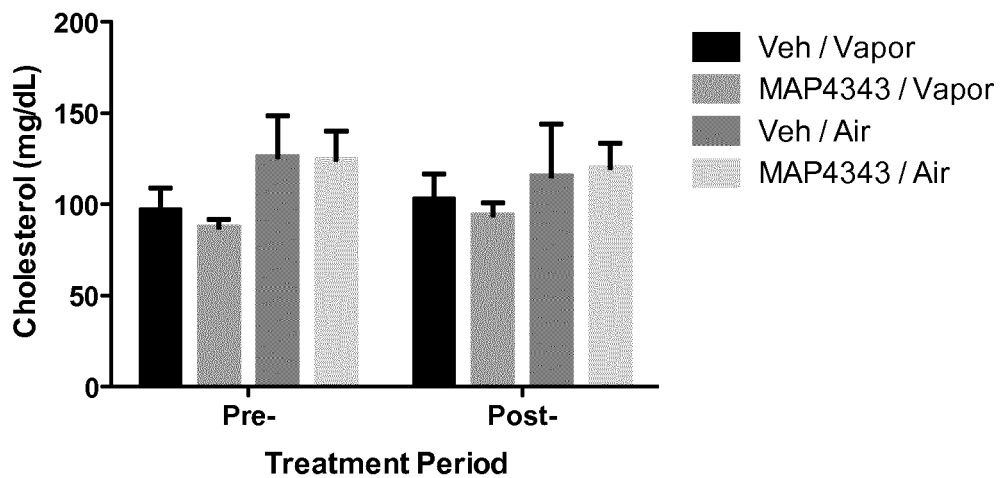
FIG. 12. Cholesterol level (mg/dL) in dependent (Vapor) and non-dependent (Air) rats before (pre-treatment) and after (post-treatment) treatment with vehicle (Veh) or MAP4343.
Figure 13:
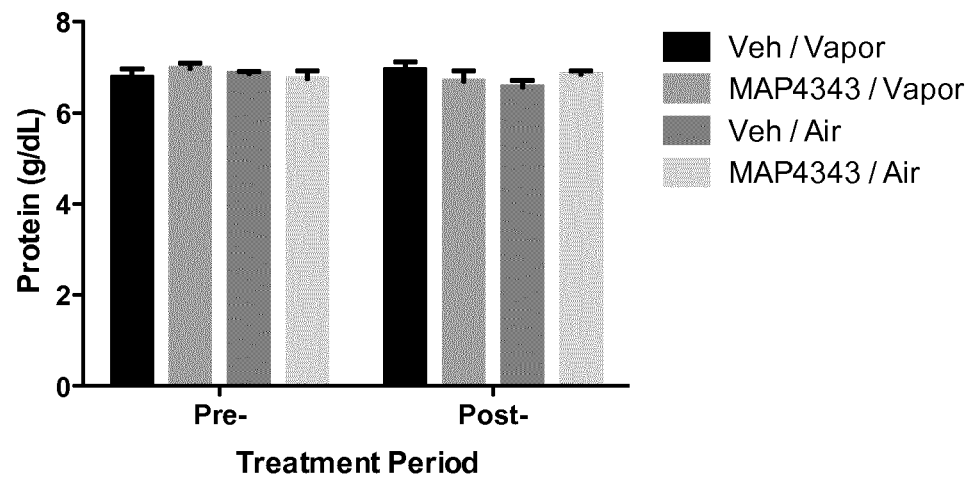
FIG. 13. Protein level (g/dL) in dependent (Vapor) and non-dependent (Air) rats before (pre-treatment) and after (post-treatment) treatment with vehicle (Veh) or MAP4343.
Figure 14:
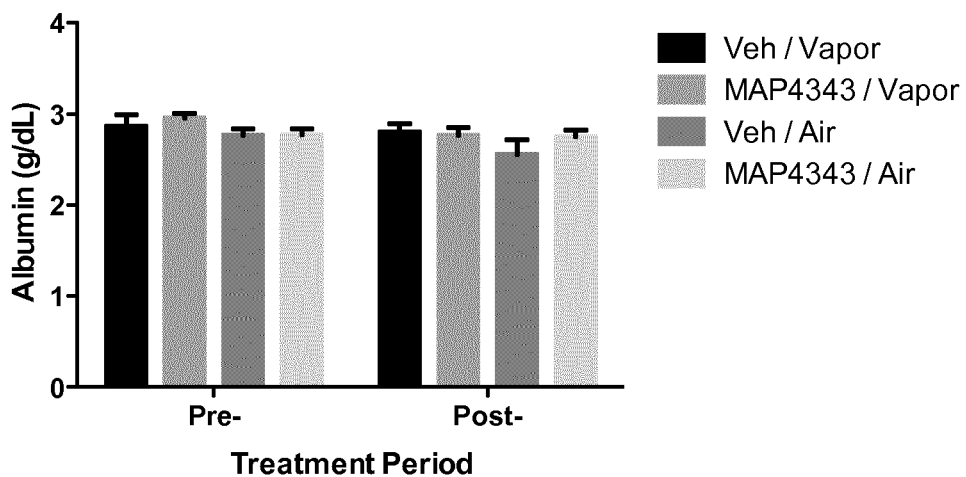
FIG. 14. Albumin level (g/dL) in dependent (Vapor) and non-dependent (Air) rats before (pre-treatment) and after (post-treatment) treatment with vehicle (Veh) or MAP4343.
Figure 15:
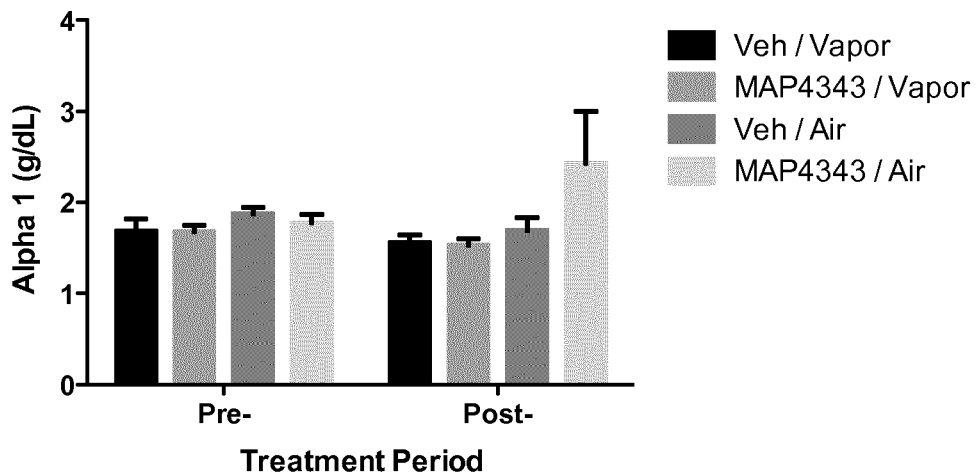
FIG. 15. Alpha1-globulin level (g/dL) in dependent (Vapor) and non-dependent (Air) rats before (pre-treatment) and after (post-treatment) treatment with vehicle (Veh) or MAP4343.
Figure 16:
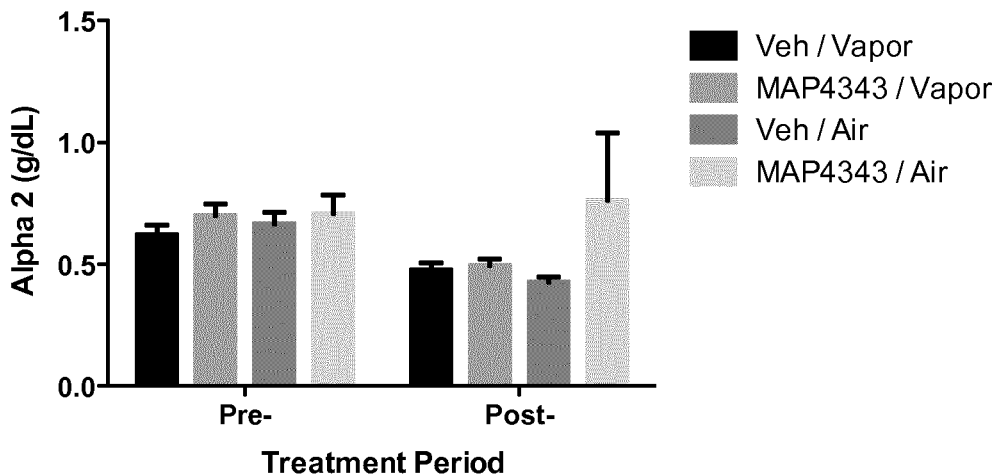
FIG. 16. Alpha2-globulin level (g/dL) in dependent (Vapor) and non-dependent (Air) rats before (pre-treatment) and after (post-treatment) treatment with vehicle (Veh) or MAP4343.
Figure 17:
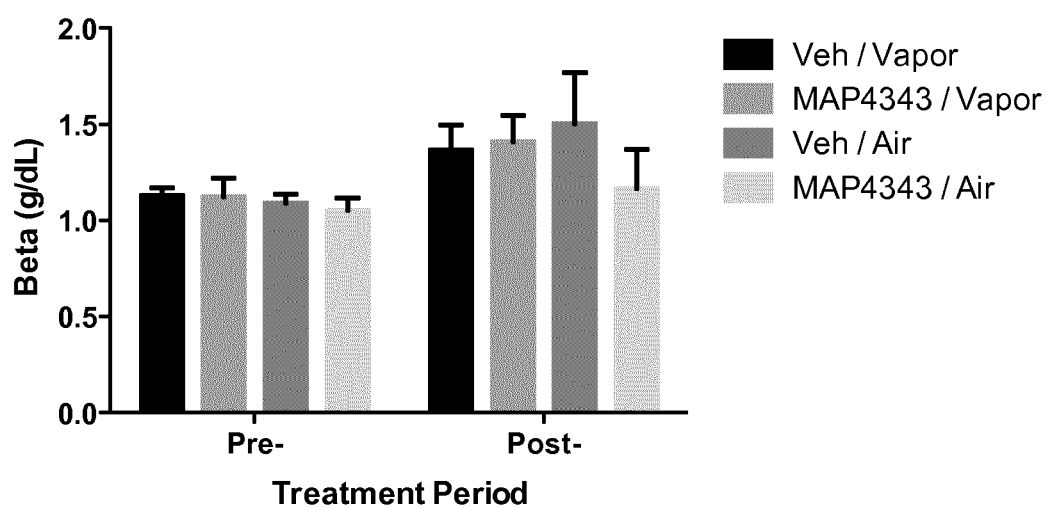
FIG. 17. beta-globulin level (g/dL) in dependent (Vapor) and non-dependent (Air) rats before (pre-treatment) and after (post-treatment) treatment with vehicle (Veh) or MAP4343.

Data were analyzed by appropriate mixed factorial ANOVA, followed Newman Keuls post hoc tests Results Behavioral Results At the end of the self-administration training the baseline of ethanol responses was 49.2±9.1 for the ethanol dependent animals and 20.3±5.9 for the non-dependent rats (see FIG. 3).

At this point the treatment started and dependent and non-dependent animals were divided into 2 groups in order to be injected with MAP4343 or its vehicle 24 hours before the test sessions. The total experiment lasted 18 days with 9 injections and 9 test sessions (see FIG. 3).

Mixed factorial ANOVA with dependence (dependent/non-dependent) and treatment (veh/MAP4343) as between factors and the time (number of test sessions) as within factor showed a significant effect of the dependence [$F(1, 15)=39.01$; $p<0.001$] and of the dependence*treatment interaction [$F(1,15)=4.50$; $p<0.05$] (see FIG. 3).

Newman Keuls post hoc test showed that the treatment with MAP4343 was able to significantly reduce operant responding for alcohol selectively in the dependent animals ($p<0.05$) starting from the test session 8 (after the injection 7) and lasting for the rest of the treatment.

Blood Results

Mixed factorial ANOVA with dependence (dependent/non-dependent) and treatment (veh/MAP4343) as between factors and the time (pre/post) as within factor showed no significant effects of dependence or treatment on any of the blood parameters investigated (See FIGS. 4 to 17).

Conclusions

Map4343 produced significant reduction of excessive alcohol drinking specifically in alcohol dependent rats and not in non-dependent rats. Efficacy of the treatment was apparent after –10 days of treatment and was maintained during the entire duration of the treatment. No effect of treatment was observed on any of the blood parameters measured. These results suggest that MAP4343, and other compounds targeting microtubules, may represent a new therapeutic strategy to reduce excessive alcohol drinking. The lack of effect of MAP4343 on any of the blood parameters measured suggests that MAP4343 treatment does not have major adverse toxic effect.

Example 5: Other Molecules According to the Invention

The indices of binding and activity are expressed as a percent of pregnenolone (PREG).

Binding (affinity) is measured by the displacement of PREG-$^3$H.

Activity is measured by the increase in optical density at 345 nm of a mixture of purified tubulin and MAP2, incubated at 37° C. in the presence of GTP.

Stimulation of neuritic sprouting is conducted on PC12 cells differentiated in the presence of NGF (10 ng/ml) and the steroid being tested (30 μM) for 3 days. For each condition, the average length of the longest 200 neurites in each cell is measured simultaneously for 3 cultures.

The results are represented in Table 5 below by one, two or three crosses (+) according to whether stimulation is lower than, equal to, or higher than that produced by PREG.

TABLE 5

Indices of binding activity of other molecules, expressed as a percent of PREG

| Steroid | Affinity | Activity | Neuritic sprouting |
|---|---|---|---|
| Pregnenolone (PREG) | 100 | 100 | ++ |
| 3β-methoxy-pregna-5-ene-20-one (3-methoxy-PREG) | 100 | 100 | +++ |
| 3β-methoxy-pregna-5-ene-20-one-17a-dichloromethyl | 53 | 113 | +++ |
| 3β-methoxy-5a- pregnane-20-one | 87 | 10 | +++ |
| 3β-methoxy-5a-pregnane-20β-ol | 65 | 65 | ++ |
| 3β-methoxy-pregna-5,14-diene-20-one | 102 | 50 | + |

These results show the effectiveness of other molecules derived from pregnenolone to stimulate the polymerization of microtubules induced by MAP2 and to stimulate neuritic sprouting. It may thus be expected that these derivatives will at least maintain the activity of 3β-methoxy-pregna-5-ene-20-one (3β-methoxy-PREG).

BIBLIOGRAPHIC REFERENCES

Addolorato G, Leggio L, Hopf F W, Diana M, Bonci A. Novel therapeutic strategies for alcohol and drug addiction: focus on GABA, ion channels and transcranial magnetic stimulation. Neuropsychopharmacology. 2012 January; 37(1):163-77.

Besheer J, Lindsay T G, O'Buckley T K, Hodge C W, Morrow A L. Pregnenolone and ganaxolone reduce operant ethanol self-administration in alcohol-preferring P rats. Alcohol Clin Exp Res. 2010 December; 34(12): 2044-52.

Gilpin N W, Smith A D, Cole M, Weiss F, Koob G F, Richardson H N. Operant behavior and alcohol levels in blood and brain of alcohol-dependent rats. Alcohol: Clin Exp Res. 2009; 33:2113-2123. [erratum: 34: 382].

Heilig M, Koob G F. A key role for corticotropin-releasing factor in alcohol dependence. Trends Neurosci. 2007; 30:399-406.

Koob G F, Le Moal M. Review. Neurobiological mechanisms for opponent motivational processes in addiction. Philos Trans R Soc Lond B Biol Sci. 2008 Oct. 12; 363(1507):3113-23.

Koob G F, Lloyd G K, Mason B J. Development of pharmacotherapies for drug addiction: a Rosetta stone approach. Nature Rev Drug Discov. 2009; 8:500-515.

Koob G F, Volkow N D. Neurocircuitry of addiction. Neuropsychopharmacology. 2010 January; 35(1):217-38.

Le Foll B, Goldberg S R. Cannabinoid CB1 receptor antagonists as promising new medications for drug dependence. J Pharmacol Exp Ther. 2005 March; 312(3):875-83.

Lowery E G, Thiele T E. Pre-clinical evidence that corticotropin-releasing factor (CRF) receptor antagonists are promising targets for pharmacological treatment of alcoholism. CNS Neurol Disord Drug Targets. 2010 March; 9(1):77-86.

Olive M F et al. Glutamatergic medications for the treatment of drug and behavioral addictions. Pharmacol Biochem Behav. 2012 February; 100(4):801-10.

US20140228336A2.

O'Dell L E, Roberts A J, Smith R T, Koob G F. Enhanced alcohol self-administration after intermittent versus continuous alcohol vapor exposure. Alcohol: Clin Exp Res. 2004; 28:1676-1682.

Richardson H N, Zhao Y, Fekete E M, Funk C K, Wirsching P, Janda K D, Zorrilla E P, Koob G F. MPZP: a novel small molecule corticotropin-releasing factor type 1 receptor ($CRF_1$) antagonist. Pharmacol Biochem Behav. 2008; 88:497-510.

Rimondini R, Arlinde C, Sommer W, Heilig M. Long-lasting increase in voluntary ethanol consumption and transcriptional regulation in the rat brain after intermittent exposure to alcohol. FASEB J. 2002; 16:27-35.

Roberts A J, Heyser C J, Koob G F. Operant self-administration of sweetened versus unsweetened ethanol: effects on blood alcohol levels. Alcohol: Clin Exp Res. 1999; 23:1151-1157.

Roberts A J, Heyser C J, Cole M, Griffin P, Koob G F. Excessive ethanol drinking following a history of dependence: animal model of allostasis. Neuropsychopharmacology. 2000; 22:581-594.

Vanyukov M M, Tarter R E, Kirisci L, Kirillova G P, Maher B S, Clark D B. Liability to substance use disorders: 1. Common mechanisms and manifestations. Neurosci Biobehav Rev. 2003 October; 27(6):507-15.

Walker B M et al. Targeting dynorphin/kappa opioid receptor systems to treat alcohol abuse and dependence. Alcohol. 2012 June; 46(4):359-70.

WO2004067010A1

WO2012160006A1

The invention claimed is:

1. A method for treating or preventing relapse of alcohol use disorder in a subject in need thereof, comprising administering to said subject a therapeutically effective amount of a compound 3-methoxy-pregna-5-ene-20-one of formula:

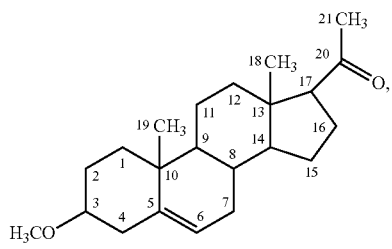

or a pharmaceutically acceptable salt thereof, wherein the subject does not have depression and has not had depression prior to said administration.

2. The method of claim 1, wherein said compound is 3β-methoxy-pregna-5-ene-20-one of formula:

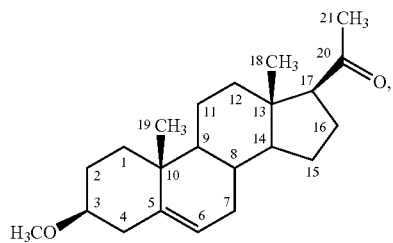 [SMILES: CO[C@H]1CC[C@@]2(C)C(=CCC3C2CC[C@@]2(C)C3CC[C@@H]2C(C)=O)C1]

or a pharmaceutically acceptable salt thereof.

3. The method of claim 1, wherein said compound or pharmaceutically acceptable salt thereof is administered via oral, intravenous, transdermal, subcutaneous, intranasal, topical, sublingual, or rectal route.

4. The method of claim 1, wherein said compound or pharmaceutically acceptable salt thereof is administered at a dose of 50 to 2000 mg/day.

5. The method of claim 1, wherein said compound or pharmaceutically acceptable salt thereof is part of a pharmaceutical composition further comprising at least one pharmaceutically acceptable excipient.

* * * * *